United States Patent [19]

Lindig et al.

[11] Patent Number: 5,030,272
[45] Date of Patent: Jul. 9, 1991

[54] SELECTIVE HERBICIDAL AGENTS CONTAINING METAMITRON IN COMBINATION WITH CERTAIN TRIAZOLINONES

[75] Inventors: Markus Lindig, Hilden; Klaus-Helmut Müller, Duesseldorf; Dieter Feucht, Monheim; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 414,154

[22] Filed: Sep. 28, 1989

[30] Foreign Application Priority Data

Oct. 5, 1988 [DE] Fed. Rep. of Germany ....... 3833801

[51] Int. Cl.$^5$ .......................................... A01N 43/707
[52] U.S. Cl. ............................................. 71/93; 71/92
[58] Field of Search ...................................... 71/92, 93

[56] References Cited

U.S. PATENT DOCUMENTS 3,847,914 11/1974 Dickore et al. ......................... 71/93
4,743,291 5/1988 Maravetz ............................... 71/92

FOREIGN PATENT DOCUMENTS 3719575 6/1987 Fed. Rep. of Germany .......... 71/92

OTHER PUBLICATIONS

CA: 90:152195 Iwai et al., 1979.
CA 87:1179Y, Schmidt et al., 1977.
CA 85:117819V, Schmidt, R. R., 1976.

Primary Examiner—Glennon H. Hollrah
Assistant Examiner—John D. Pak
Attorney, Agent, or Firm—Sprung Horn Kramer & Woods

[57] ABSTRACT

A method of selectively combating weeds in beet crops which comprises applying to the beet field before or after emergence of the plants a composition comprising
(a) 4-amino-3-methyl-6-phenyl-1,2,4-triazin-5-(4H)-one (metamitron) of the formula

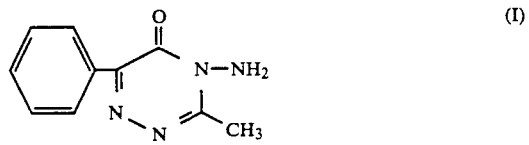

(I)

and
(b) at least one 4-amino-1-carbamoyl-5-methyl-1,2,4-(1H)-triazolin-5-one substituted on the amide nitrogen atom, of the formula

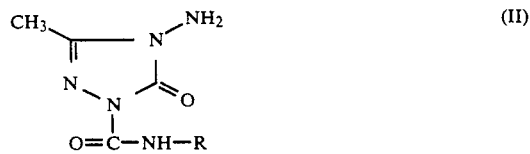

(II)

in which
R represents straight-chain or branched $C_1$-$C_{10}$-alkyl (which can optionally be substituted by halogen), or represents straight-chain or branched $C_3$-$C_8$-alkenyl or $C_3$-$C_8$-alkinyl, or represents $C_3$-$C_6$-cycloalkyl (which can optionally be substituted by methyl or trifluoromethyl).

6 Claims, No Drawings

SELECTIVE HERBICIDAL AGENTS CONTAINING METAMITRON IN COMBINATION WITH CERTAIN TRIAZOLINONES

The invention relates to new herbicidal synergistic active compound combinations which consist of metamitron on the one hand and certain triazolinones on the other hand and can be used with particular advantage for selectively combating weeds in beet crops, beet weeds which are difficult to combat, such as Galium and Mercurialis, also being reliably combated.

It has already been disclosed that 4-amino-3-methyl-6-phenyl-1,2,4-triazin-5(4H)-one (common name: metamitron) can be used as a selective herbicide in beet crops (compare DE-OS (German Published Specification) 2,224,161 and US-PS 3,847,914). The active compound metamitron has a very good herbicidal action and can be used selectively in sugar beet, and has achieved practical importance in this indication.

However, the action of metamitron against certain weeds is not always adequate. Thus, Galium aparine is combated only at increased dosages, and Mercurialis annua is virtually not combated at all.

It has now been found, surprisingly, that the new active compound combinations consisting of (1) 4-amino-3-methyl-6-phenyl-1,2,4-triazin-5(4H)-one (metamitron) of the formula (I)

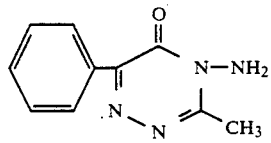

and (2) at least one 4-amino-1-carbamoyl-3-methyl-1,2,4-(1H)-triazolin-5-one substituted on the amide nitrogen atom, of the general formula (II)

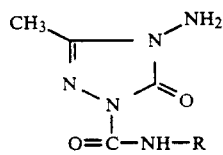

in which represents straight-chain or branched $C_1$–$C_{10}$-alkyl (which can optionally be substituted by halogen), or represents straight-chain or branched $C_3$–$C_8$-alkenyl or $C_3$–$C_8$-alkinyl, or represents $C_3$–$C_6$-cycloalkyl (which can optionally be substituted by methyl or trifluoromethyl), have a particularly high herbicidal activity without damaging beet crops.

Preferred active compounds of the formula (II) are those compounds of the general formula (II) wherein R represents $C_3$–$C_8$-alkyl which is optionally substituted by fluorine or chlorine, or represents $C_3$–$C_5$-alkenyl, or represents $C_3$–$C_5$-alkinyl, or represents $C_3$–$C_6$-cycloalkyl which is optionally substituted by trifluoromethyl.

Particularly preferred active compounds of the formula (II) are those compounds of the general formula (II) wherein R has the following meanings:

| | |
|---|---|
| R = —C(CH$_3$)$_3$ | (II-1) |
| R = —C(CH$_3$)$_2$—CH$_2$—Cl | (II-2) |
| R = —CH—CH(CH$_3$)$_2$<br>    \|<br>    CH$_3$ | (II-3) |
| R = —C(CH$_3$)$_2$—CH$_2$—CH$_3$ | (II-4) |
| R = —C(CH$_3$)$_2$—CH$_2$—F | (II-5) |
| R = —C(CH$_3$)$_2$—C≡CH | (II-6) |
| R = —C(CH$_3$)$_2$—C$_3$H$_7$-n | (II-7) |
| R = —C(CH$_3$)$_2$—CH(CH$_3$)$_2$ | (II-8) |
| R = —C(CH$_3$)$_2$—C$_4$H$_9$-n | (II-9) |
| R = —C(CH$_3$)$_2$—CF$_3$ | (II-10) |

Surprisingly, the herbicidal activity of the active compound combination according to the invention is considerably higher than the sum of the actions of the individual active compounds. A true synergistic effect which cannot be predicted, and not only a supplementation of the action, is therefore present. The new active compound combinations, in the same way as metamitron (I), are tolerated very wall in beet crops, the new active compound combinations also being outstanding at combating the "problem weeds" Galium and Mercurialis which are otherwise difficult to combat. The new active compound combinations thus represent a valuable enrichment of beet herbicides.

Examples which may be mentioned of weeds which occur in general as contamination in beet crops and can be combated reliably by the active compound combinations according to the invention are:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea and Mercurialis; and Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

However, the use of the active compound combinations according to the invention is in no way restricted to these genera, but also extends in the same manner to other plants.

As already stated, the active compound combinations according to the invention have a very good tolerance towards beet crops and an outstanding action against broad-leaved weeds and gramineous weeds; their use as selective beet herbicides is therefore particularly preferred.

The synergistic effect of the active compound combinations according to the invention is particularly strongly pronounced under certain concentration ratios. However, the weight ratios of the active compounds in the active compound combinations can be varied within relatively wide ranges. In general, 0.01 to 10 parts by weight, preferably 1.0 to 5 parts by weight and particularly preferably 0.2 to 1.2 parts by weight, of active compound from the active compound group (II) are present per part by weight of active compound of the formula (I).

The active compound combinations according to the invention can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 1.0 and 95 per cent by weight of active compound combination, preferably between 0.5 and 90%.

The active compound combinations according to the invention are in general used in the form of finished formulations. However, the active compounds contained in the active compound combinations can also be mixed as individual formulations when used, that is to say used in the form of tank mixes.

The new active compound combinations can furthermore be used as such or in their formulations as a mixture with other known beet herbicides, finished formulations or tank mixes again being possible. Mixtures with other known active compounds, such as fungicides, insecticides, acaricides, nematicides, bird repellents, growth factors, plant nutrients and agents which improve soil structure, are also possible. For certain application purposes, in particular in the post-emergence method, it can furthermore be advantageous to include mineral or vegetable oils which are tolerated by plants (for example the commercial preparation "Sun Oil 11E") or ammonium salts, such as, for example, ammonium sulphate or ammonium thiocyanate, as further additives in the formulations.

The new active compound combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, dusting or scattering.

The amounts of the active compound combinations according to the invention applied can be varied within a certain range; they depend inter alia on the weather and on soil factors. In general, the amounts applied are between 0.05 and 15 kg of active compound combination per ha, preferably between 0.5 and 10 kg/ha and particularly preferably between 1.5 and 6 kg/ha.

The active compound combinations according to the invention can be applied either before or after emergence of the plants, that is to say by the pre-emergence or by the post-emergence method.

The good herbicidal action of the new active compound combinations can be seen from the following examples. Whilst the individual active compounds show weaknesses in herbicidal action, the combinations exhibit a very broad herbicidal action which extends beyond a simple summation of the action.

A synergistic effect is always present with herbicides if the herbicidal action of the active compound combination is greater than that of the individual active compounds applied.

The action to be expected for a given combination of two herbicides can be calculated as follows (compare COLBY, S. R., "Calculating synergistic and antagonistic responses of herbicide combinations", Weeds 15, pages 20-22, 1967):

If X=% damage by herbicide A when p kg/ha is the amount applied and

Y=% damage by herbicide B when q kg/ha is the amount applied and

E=the expected damage of he herbicides A and B when p and q kg/ha is the amount applied, then $$E = X + Y - \frac{X \cdot Y}{100}.$$

If the actual damage is greater than calculated, the combination is superadditive in its action, that is to say it exhibits a synergistic effect.

The following examples show that the herbicidal action found for the active compound combinations according to the invention on weeds is greater than that calculated, that is to say that the new active compound combinations have a synergistic action.

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound or active compound combination is mixed with the stated amount of solvent, the stated amount of emulsifier is added and the concentrate is diluted with water to the desired concentration.

Seeds of the test plants are sown in normal soil and, after 24 hours, watered with the preparation of the active compound. In this connection it is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

The active compounds, amounts applied and results can be seen from the following Tables A-1, A-2, A-3 and A-4.

TABLE A-1

| Active compound or active compound combination | Amount applied g/ha | pre-emergence test/greenhouse Action or damage in % | | | |
|---|---|---|---|---|---|
| | | Galium | | Sugar beet | |
| | | found* | calc.* | found* | calc.* |
| (I) | 2000 | 0 | | 0 | |
| - known - (II-4) | 1000 | 0 | | 0 | |
| | 2000 | 70 | | 0 | |
| - known - | 1000 | 0 | | 0 | |
| (I) + (II-4) according to the invention | 1000 + 1000 | 90 | 0 | 0 | 0 |

TABLE A-1-continued pre-emergence test/greenhouse (I) = metamitron
(II-4) = compound of the formula (II) where R = —C(CH₃)₂—CH₂—CH₃
*found = damage found (in per cent)
*calc. = damage calculated according to the COLBY formula (in per cent)

TABLE A-2

| Active compound or active compound combination | Amount applied g/ha | pre-emergence test/greenhouse Action or damage in % | | | |
|---|---|---|---|---|---|
| | | Galium | | Sugar beet | |
| | | found* | calc.* | found* | calc.* |
| (I) | 500 | 0 | | 0 | |
| - known - (II-5) | 250 | 0 | | 0 | |
| | 500 | 0 | | 0 | |
| - known - | 250 | 0 | | 0 | |
| (I) + (II-5) according to the invention | 250 + 250 | 70 | 0 | 0 | 0 |

(I) = metamitron
(II-5) = compound of the formula (II) where R = —C(CH₃)₂—CH₂—F
*found = damage found (in per cent)
*calc. = damage calculated according to the COLBY formula (in per cent)

TABLE A-3

| Active compound or active compound combination | Amount applied g/ha | pre-emergence test/greenhouse Action or damage in % | | | |
|---|---|---|---|---|---|
| | | Mercurialis | | Sugar beet | |
| | | found* | calc.* | found* | calc.* |
| (I) | 500 | 0 | | 0 | |
| - known - (II-5) | 250 | 0 | | 0 | |
| | 500 | 60 | | 0 | |
| - known - | 250 | 20 | | 0 | |
| (I) + (II-5) according to the invention | 250 + 250 | 100 | 20 | 0 | 0 |

(I) = metamitron
(II-5) = compound of the formula (II) where R = —C(CH₃)₂—CH₂—F
*found = damage found (in per cent)
*calc. = damage calculated according to the COLBY formula (in per cent)

TABLE A-4

| Active compound or active compound combination | Amount applied g/ha | pre-emergence test/greenhouse Action or damage in % | | | |
|---|---|---|---|---|---|
| | | Avena | | Sugar beet | |
| | | found* | calc.* | found* | calc.* |
| (I) | 1000 | 0 | | 0 | |
| - known - (II-6) | 500 | 0 | | 0 | |
| | 1000 | 80 | | 0 | |
| - known - | 500 | 0 | | 0 | |
| (I) + (II-6) according to the invention | 500 + 500 | 90 | 0 | 0 | 0 |

(I) = metamitron
(II-6) = compound of the formula (II) where R = —C(CH₃)₂—C≡CH
*found = damage found (in per cent)
*calc. = damage calculated according to the COLBY formula (in per cent)

EXAMPLE B

Post-emergence test

Solvent: 5 parts by weight of acetone

Emulsifier: 1 pat by weight of alkylaryl polyglycol ether

To produce a suitable preparation of active compound, 1 part by weight of active compound or active compound combination is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 500 l of water/ha. After three weeks, the degree of damage to the plants is rated in % damage in comparison to the development of the untreated control. The figures denote:

0% = no action (like untreated control)
100% = total destruction

The active compounds, amounts applied and results can be seen from the following Tables B-1 and B-2.

TABLE B-1

| Active compound or active compound combination | Amount applied g/ha | pre-emergence test/greenhouse Action or damage in % | | | |
|---|---|---|---|---|---|
| | | Alopecurus | | Sugar beet | |
| | | found* | calc.* | found* | calc.* |
| (I) | 2000 | 70 | | 0 | |
| - known - | 1000 | 60 | | 0 | |
| (II-1) | 2000 | 90 | | 0 | |
| - known - | 1000 | 80 | | 0 | |
| (I) + (II-1) according to the invention | 1000 + 1000 | 100 | 92 | 0 | 0 |

(I) = metamitron
(II-1) = compound of the formula (II) where R = —C(CH₃)₃
*found = damage found (in per cent)
*calc. = damage calculated according to the COLBY formula (in per cent)

TABLE B-2

| Active compound or active compound combination | Amount applied g/ha | pre-emergence test/greenhouse Action or damage in % | | | |
|---|---|---|---|---|---|
| | | Alopecurus | | Sugar beet | |
| | | found* | calc.* | found* | calc.* |
| (I) | 1000 | 10 | | 0 | |
| - known - | 500 | 0 | | 0 | |
| | 250 | 0 | | 0 | |
| (II-5) | 1000 | 60 | | 0 | |
| - known - | 500 | 10 | | 0 | |
| | 250 | 0 | | 0 | |
| (I) + (II-5) according to the invention | 500 + 500 250 + 250 | 70 50 | 10 0 | 0 | 0 |

(I) = metamitron
(II-5) = compound of the formula (II) where R = —C(CH₃)₂—CH₂—F
*found = damage found (in per cent)
*calc. = damage calculated according to the COLBY formula (in per cent)

The active compound of the formula (I) is known (DE-OS (German Published Specification) 2,224,161 and US-PS 3,847,914). The active compounds of the formula (II) are the subject of German Patent Applications P 37 19 575.1 of June 12, 1987, and P 38 03 523.5 of Feb. 5, 1988, both corresponding to U.S. Patent Appln. Ser. No. 200,995 filed May 31, 1988, now pending.

The active compounds of the general formula (II)

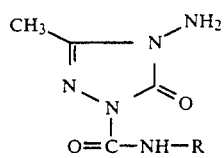

in which
R represents straight-chain or branched C₁–C₁₀-alkyl (which can optionally be substituted by halogen), or represents straight-chain or branched C₃–C₈-alkenyl or C₃–C₈-alkinyl, or represents C₃–C₆-cycloalkyl (which can optionally be substituted by methyl or trifluoromethyl),
can be prepared by a process in which either
(a) 4-amino-3-methyl-1,2,4-(1H)-triazolin-5-one of the formula (III)

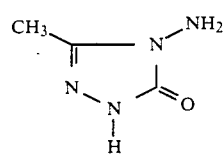

is reacted with isocyanates of the formula (IV)

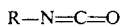

wherein R has the meanings given in the case of formula (II), if appropriate in the presence of an inert organic solvent as a diluent (such as, for example, acetonitrile) and if appropriate in the presence of a basic reaction auxiliary (such as, for example, triethylamine) at temperatures between 0° C. and 150° C., preferably between 20° C. and 100° C., in general 1.0 to 2.0 mols, preferably 1.0 to 1.5 mols, of isocyanate (IV) and if appropriate 0.001 to 2.0 mols, preferably 0.01 to 1.0 mol, of reaction auxiliary being employed per mol of starting substance (III), or
(b) triazolinones of the formula (V)

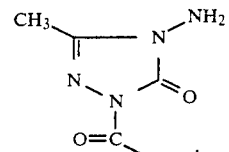

wherein R¹ represents C₁–C₄-alkyl phenyl or benzyl, are reacted with amines of the formula (VI)

wherein R has the meanings given above in the case of formula (II), if appropriate in the presence of an inert organic solvent as a diluent (such as, for example, tetrahydrofuran and dioxane) and if appropriate in the presence of a basic reaction auxiliary (such as, for example, sodium hydroxide, potassium carbonate, pyridine or triethylamine) at temperatures between 0° C. and 120° C., preferably between 20° C. and 50° C., in general 1.0 to 5.0 mols, preferably 1.0 to 2.5 mols, of amine (VI) and if appropriate 1.0 to 2.0 mols, preferably 1.0 to 1.2 mols, of reaction auxiliary being employed per mol of starting substance (V) (compare also the preparation examples).

4-Amino-3-methyl-1,2,4-(1H)-triazolin-5-one (III) is known (compare Europ. J. Med. Chem.; Chim. Ther. 18, 215 -220 [1983]).

The starting substances of the formula (V) are not yet known; they can be prepared by a method analogous to the preparation of closely related compounds which are already known (compare, for example, J. Heterocycl. Chem. 17, 1691–1696 [1980]) by a process in which 4-amino-3-methyl-1,2,4-(1H)-triazolin-5-one (III) is reacted with chloroformic acid esters of the formula (VII)

$$R^1-O-CO-Cl \quad (VII)$$

wherein $R^1$ represents $C_1-C_4$-alkyl, phenyl or benzyl, if appropriate in the presence of a diluent (for example tetrahydrofuran) and if appropriate in the presence of a reaction auxiliary (such as, for example, potassium t-butylate or sodium hydride) at temperatures between −20° C. and +40° C. (compare also the preparation examples).

Preparation Examples

Example 1

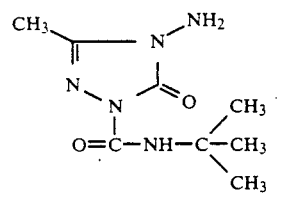
(II-1)

3.6 g (0.036 mol) of t-butyl isocyanate and 1.0 g of diazabicycloundecene (DBU) are added to a solution of 3.42 g (0.03 mol) of 4-amino-3-methyl-1,2,4-(1H)-triazolin-5-one in 80 ml of absolute acetonitrile, mixture is stirred at 20° C. for 2 hours and concentrated in vacuo, the residue is taken up in methylene chloride, the mixture is washed with water, dried over sodium sulphate and concentrated in vacuo and the residue is crystallized by trituration with diethyl ether. 5.0 g (78.3% of theory) of 4-amino-1-(N-t-butylcarbamoyl)-3-methyl-1,2,4-triazolin-5-one of melting point 132° C. are obtained.

The following substituted triazolinones of the general formula (II) are obtained in a corresponding manner and in accordance with the general instructions on the preparation:

Example 2

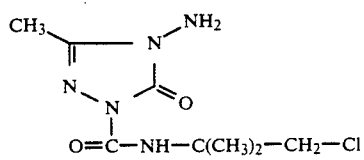
(II-2)

Melting point: 118° C.

Example 3

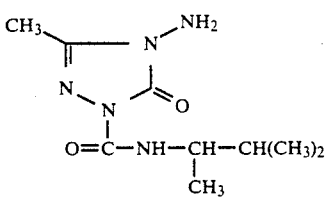
(II-3)

Melting point: 103° C.

Example 4

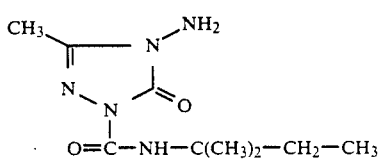
(II-4)

Melting point: 99° C.

Example 5

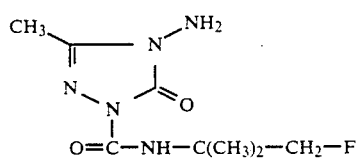
(II-5)

Melting point: 1788° C.

Example 6

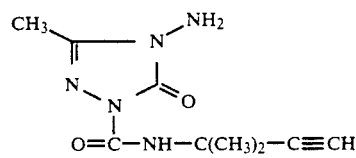
(II-6)

Melting point: 119° C.

Example 7

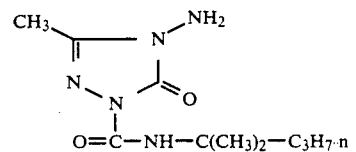
(II-7)

Melting point: 110° C.

Example 8

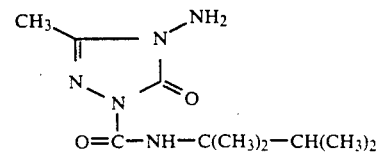
(II-8)

Melting point: 134° C.

Example 9

[Structure (II-9): 3-methyl-1,2,4-triazolin-5-one with 4-NH₂ and N1-C(O)-NH-C(CH₃)₂-C₄H₉-n]

Refractive index: Nhu $22_D = 1.4891$

Example 10

[Structure (II-10): analogous with N1-C(O)-NH-C(CH₃)₂-CF₃]

Melting point: 150° C.

Example 11

[Structure (II-11): analogous with N1-C(O)-NH-cyclohexyl]

Melting point: 148° C.

Example 12

[Structure (II-12): analogous with N1-C(O)-NH-cyclopentyl]

Melting point: 94° C.

Example 13

[Structure (II-13): analogous with N1-C(O)-NH-cyclopropyl]

Melting point: 134° C.

Example 14

[Structure (II-14): analogous with N1-C(O)-NH-(4-CF₃-cyclohexyl)]

Melting point: 162° C.

Example 15

[Structure (II-15): analogous with N1-C(O)-NH-(1-methylcyclopentyl)]

Melting point: 145° C.

Example of a starting substance of the formula (V)

[Structure (V-1): analogous with N1-C(O)-O-phenyl]

2.7 g (0.024 mol) of potassium t-butylate are added to a solution of 2.3 g (0.02 mol) of 4-amino-3-methyl-1,2,4-(1H)-triazolin-5-one in 25 ml of absolute tetrahydrofuran, the mixture is stirred at 20° C. for one hour, 3.1 g (0.02 mol) of phenyl chloroformate are then added dropwise, while stirring, the mixture is stirred at room temperature for 12 hours and then brought to pH 5 with glacial acetic acid and concentrated in vacuo, the residue is taken up in chloroform, the mixture is washed with water, dried over sodium sulphate and concentrated in vacuo and the residue is crystallized by trituration with ether.

1.1 g (23.5% of theory) of 4-amino-3-methyl-1-phenoxycarbonyl-1,2,4-triazolin-5-one of melting point 175° C. are obtained.

It is understood that the specification and examples are illustrative but not limitative of the present invention and that other embodiments within the spirit and scope of the invention will suggest themselves to those skilled in the art.

We claim:

1. A herbicidal composition consisting essentially of a synergistically herbicidally effective amount of a mixture of
   (a) 4-amino-3-methyl-6-phenyl-1,2,4-triazin-5-(4H)-one (metamitron) of the formula

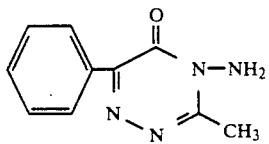

and (b) at least one 4-amino-1-carbamoyl-3-methyl-1,2,4-(1H)-triazolin-5-one formula

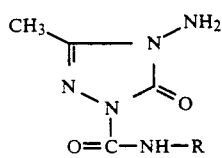

in which

R represents straight-chain or branched $C_1$-$C_{10}$-alkyl, or a halogen substituted straight-chain or branched $C_1$-$C_{10}$-alkyl, or represents straight-chain or branched $C_3$-$C_8$-alkenyl or $C_3$-$C_8$-alkinyl.

2. A herbicidal composition according to claim 1, wherein the weight ratio of (I) to (II) is between about 1:0.01 and 1:10.

3. A herbicidal composition according to claim 1, wherein the weight ratio of (I) to (II) is between about 1:1.0 and 1:5.

4. A herbicidal composition according to claim 1, in which

R represents $C_3$-$C_8$-alkyl which is optionally substituted by fluorine or chlorine, or represents $C_3$-$C_5$-alkenyl, or represents $C_3$-$C_5$-alkinyl.

5. A herbicidal composition according to claim 1, in which

R is selected from the group consisting of:
—C(CH$_3$)$_3$, —C(CH$_3$)$_2$—CH$_2$—Cl,

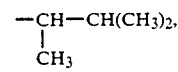

—C(CH$_3$)$_2$—CH$_2$—CH$_3$, —C(CH$_3$)$_2$—CH$_2$—F,
—C(CH$_3$)$_2$—C≡CM,
—C(CH$_3$)$_2$—C$_3$H$_7$—n, —C(CH$_3$)$_2$—CH(CH$_3$)$_2$,
—C(CH$_3$)$_2$—C$_4$H$_9$—n, and —C(CH$_3$)$_2$—CF$_3$, 6. A method of selectively combating weeds in beet crops which comprises applying to the beet field before or after emergence of the plates a composition consisting essentially of a synergistically herbicidally effective amount of a mixture according to claim 1.

* * * * *

UNITED STATES PATENT AND TRADEMARK OFFICE
CERTIFICATE OF CORRECTION

PATENT NO. : 5,030,272

DATED : July 9, 1991

INVENTOR(S) : Lindig et al.

It is certified that error appears in the above-identified patent and that said Letters Patent is hereby corrected as shown below:

Col. 13, line 11    Before " formula " insert -- substituted on the amide nitrogen atom, of the --

Col. 14, line 3    Delete " 1:1.0 " and substitute -- 1:0.1 --

Signed and Sealed this

Twenty-seventh Day of April, 1993

*Attest:*

MICHAEL K. KIRK

*Attesting Officer*    *Acting Commissioner of Patents and Trademarks*